United States Patent
Shammaa

(10) Patent No.: US 12,173,272 B2
(45) Date of Patent: Dec. 24, 2024

(54) APPARATUS AND METHOD FOR ISOLATING STEM CELLS

(71) Applicant: Cell Technologies, Inc., Sacramento, CA (US)

(72) Inventor: Riam Shammaa, Toronto (CA)

(73) Assignee: Cell Technologies, Inc., Sacramento, CA (US)

(*) Notice: Subject to any disclaimer, the term of this patent is extended or adjusted under 35 U.S.C. 154(b) by 0 days.

(21) Appl. No.: 18/472,301

(22) Filed: Sep. 22, 2023

(65) Prior Publication Data
US 2024/0010967 A1 Jan. 11, 2024

Related U.S. Application Data

(62) Division of application No. 16/688,543, filed on Nov. 19, 2019, now abandoned.
(Continued)

(51) Int. Cl.
*C12M 1/00* (2006.01)
*A01N 1/02* (2006.01)
(Continued)

(52) U.S. Cl.
CPC ........... *C12M 47/04* (2013.01); *A01N 1/0242* (2013.01); *A61M 1/3417* (2014.02);
(Continued)

(58) Field of Classification Search
None
See application file for complete search history.

(56) References Cited

U.S. PATENT DOCUMENTS

| | | |
|---|---|---|
| 2007/0025883 A1 | 2/2007 | Tai et al. |
| 2015/0087016 A1 | 3/2015 | Takagi |
| 2020/0298150 A1 | 9/2020 | Kamba |

FOREIGN PATENT DOCUMENTS

| | | | | |
|---|---|---|---|---|
| CA | 2546084 A1 | * | 11/2006 | ............. A61K 38/28 |
| JP | 2008022822 A | | 2/2008 | |

(Continued)

*Primary Examiner* — William H. Beisner
(74) *Attorney, Agent, or Firm* — Foley IP Law, PLLC

(57) ABSTRACT

An apparatus for isolating stems cells from extracted mammalian tissue comprising:
a portable hollow casing having fixed dimensions and a sized internal spatial volume;
a filter housed and contained within said sized internal spatial volume, wherein said filter captures particles in said extracted mammalian tissue having a diameter of about 5 to 10 microns or more and allows particles in said extracted mammalian tissue having a diameter of less than about 5 to 10 microns to pass through;
a first channel to which a container holding said extracted mammalian tissue can attach, and through which said extracted mammalian tissue is input into the hollow casing;
wherein a stem cell collection chamber can attach to said first channel, and the particles having a diameter of about 5 to 10 microns or more are output from the hollow casing through said first channel and collected in the stem cell collection chamber; and
a second channel to which a remnant collection chamber can attach, and through which the particles having a diameter of less than about 5 to 10 microns are output from the hollow casing and collected in the remnant collection chamber.

8 Claims, 13 Drawing Sheets

Related U.S. Application Data

(60) Provisional application No. 62/797,241, filed on Jan. 26, 2019.

(51) Int. Cl.
    *A61M 1/34*     (2006.01)
    *C12M 1/26*     (2006.01)
    *C12N 5/00*     (2006.01)
    *C12N 5/0775*     (2010.01)
    *C12N 5/0783*     (2010.01)

(52) U.S. Cl.
    CPC .......... *A61M 1/3496* (2013.01); *C12M 33/10* (2013.01); *C12N 5/0087* (2013.01); *C12N 5/0636* (2013.01); *C12N 5/0665* (2013.01); *C12N 5/0668* (2013.01)

(56) References Cited

FOREIGN PATENT DOCUMENTS

| | | | | |
|---|---|---|---|---|
| JP | 2010246446 A | * | 11/2010 | ............ C12M 47/04 |
| WO | WO-2015056997 A1 | * | 4/2015 | ............ C12M 33/14 |

* cited by examiner

APPARATUS AND METHOD FOR ISOLATING STEM CELLS

CROSS-REFERENCE TO RELATED APPLICATION

This application is a divisional of U.S. patent application Ser. No. 16/688,543, filed Nov. 19, 2019, entitled "Apparatus and Method for Isolating Stem Cells", which claims the benefit of U.S. Provisional Application No. 62/797,241, filed Jan. 26, 2019, entitled "Apparatus and Method for Isolating Stem Cells", the entirety each is hereby incorporated by reference herein.

FIELD OF THE INVENTION

The present invention relates to isolating stem cells, and more specifically, to an apparatus and method for isolating stem cells from a sample.

BACKGROUND ART

Stem cells are biological cells that can differentiate into other types of cells and can divide to produce more of the same type of stem cells. They are found in multicellular organisms, including mammals such as humans. In mammals, adult stem cells can act as a repair system for the body by replenishing adult tissues, thus giving rise to use of stem cells in medical therapies such as bone marrow transplantation for the treatment of leukemia and lymphoma.

Mesenchymal stem cells (MSCs) can differentiate into the cells that make up bone, cartilage, tendons, and ligaments, as well as muscle, neural and other progenitor tissues. As such, mesenchymal stem cells have been the main type of stem cells studied in the treatment of diseases affecting these tissues. Hematopoietic stem cells (HSCs) can differentiate into cells that make up blood including red blood cells, white blood cells and platelets. As such, Hematopoietic stem cells have been the main type of stem cells studied in the treatment of diseases affecting the blood, such as leukemia.

Stem cell therapy is the use of the harvested stem cells to treat or prevent a disease or condition. Adult stem cell treatments have been successfully used to treat leukemia and related bone/blood cancers through bone marrow transplants. Bone marrow transplant is a form of stem cell therapy that has been used in treating several other conditions including liver cirrhosis, chronic limb ischemia and end stage heart failure. Adult stem cells are also used in veterinary medicine to treat tendon and ligament injuries in horses.

In stem cell therapy, healthy and functional stem cells must be harvested from a donor, who may or may not be the same person as the patient to be treated. There are several well-known sources of adult stem cells, also called somatic stem cells, in humans:

a. Bone marrow, which require extraction by harvesting, that is, drilling into bone (typically the femur or iliac crest);
b. Adipose tissue (fat cells), which require extraction by liposuction; and
c. Blood, which requires extraction through apheresis, wherein blood is drawn from the donor (similar to a blood donation), centrifuged to separate components and, after selected components are drawn off, returned to the donor.

Stem cells can also be taken from umbilical cord blood just after birth. Of all stem cell types, autologous harvesting, where the cells are obtained from the patient's own body, involves the least risk of rejection.

Prior to treatment of the patient, the donor stem cells must be isolated from the bone marrow, adipose tissue, blood or other tissue which was extracted from the donor. Current methods for isolating stem cells from extracted tissue are based on centrifugation. Specifically, any solid-liquid mixture or liquid that may contain stem cells is subjected to centrifugation, and the application of centrifugal force attempts to separate particles according to their size, shape, density and/or viscosity. Centrifugation is widely used and often effective in many biotechnology applications. However, it does not isolate stem cells efficiently. Instead, centrifugation merely sends any nucleated cells or heavy cells to the bottom of the centrifugation tube. This method does not isolate or select stem cells in an efficient manner.

Furthermore, devices used for stem cell isolation tend to be relatively large, cumbersome and difficult to transport. For example, centrifuge machines are not easily portable.

It would be beneficial to develop a method, and perhaps an apparatus, by which stem cells can be isolated from extracted tissue in a cost-effective and efficient manner.

Furthermore, it would be beneficial to develop an apparatus which is easy to use, relatively small in size and easily portable.

SUMMARY OF THE INVENTION

In one aspect, the present invention comprises an apparatus for isolating stems cells from extracted mammalian tissue comprising:
  a portable hollow casing having fixed dimensions and a sized internal spatial volume;
  a filter housed and contained within said sized internal spatial volume, wherein said filter captures particles in said extracted mammalian tissue having a diameter of about 5 to 10 microns or more and allows particles in said extracted mammalian tissue having a diameter of less than about 5 to 10 microns to pass through;
  a first channel to which a container holding said extracted mammalian tissue can attach, and through which said extracted mammalian tissue is input into the hollow casing;
  wherein a stem cell collection chamber can attach to said first channel, and the particles having a diameter of about 5 to 10 microns or more are output from the hollow casing through said first channel and collected in the stem cell collection chamber; and
  a second channel to which a remnant collection chamber can attach, and through which the particles having a diameter of less than about 5 to 10 microns are output from the hollow casing and collected in the remnant collection chamber.

In another aspect, the present invention provides a method for isolating stem cells from extracted mammalian tissue comprising:
  (a) providing a container holding said extracted mammalian tissue;
  (b) attaching the container holding said extracted mammalian tissue to an apparatus for isolating stems cells from extracted mammalian tissue comprising:
  a portable hollow casing having fixed dimensions and a sized internal spatial volume;
  a filter housed and contained within said sized internal spatial volume, wherein said filter captures particles in said extracted mammalian tissue having a diameter of about 5 to 10 microns or more and allows particles in said extracted mammalian tissue having a diameter of less than about 5 to 10 microns to pass through;

a first channel to which the container holding said extracted mammalian tissue can attach, and through which said extracted mammalian tissue is input into the hollow casing;

wherein a stem cell collection chamber can attach to said first channel, and the particles having a diameter of about 5 to 10 microns or more are output from the hollow casing through said first channel and collected in the stem cell collection chamber; and a second channel to which a remnant collection chamber can attach, and through which the particles having a diameter of less than about 5 to 10 microns are output from the hollow casing and collected in the remnant collection chamber;

wherein the hollow casing comprises a top portion and a bottom portion which are detachable from each other;

wherein the filter is inserted between the top portion and the bottom portion;

(c) causing the extracted mammalian tissue to move from the container holding said extracted mammalian tissue, through the first channel, into the hollow casing and into contact with the filter;

(d) allowing particles having a diameter of about 5 to 10 microns or more to be captured by the filter, move out of the hollow casing through the first channel and into the stem cell collection chamber; and (e) allowing particles having a diameter of less than about 5 to 10 microns to pass through the filter, move out of the hollow casing through the second channel and into the remnant collection chamber.

BRIEF DESCRIPTION OF THE DRAWINGS

Advantages of the invention will become apparent upon reading the following description of the drawings and description of the invention.

DETAILED DESCRIPTION OF THE PREFERRED EMBODIMENTS

Figure 1:
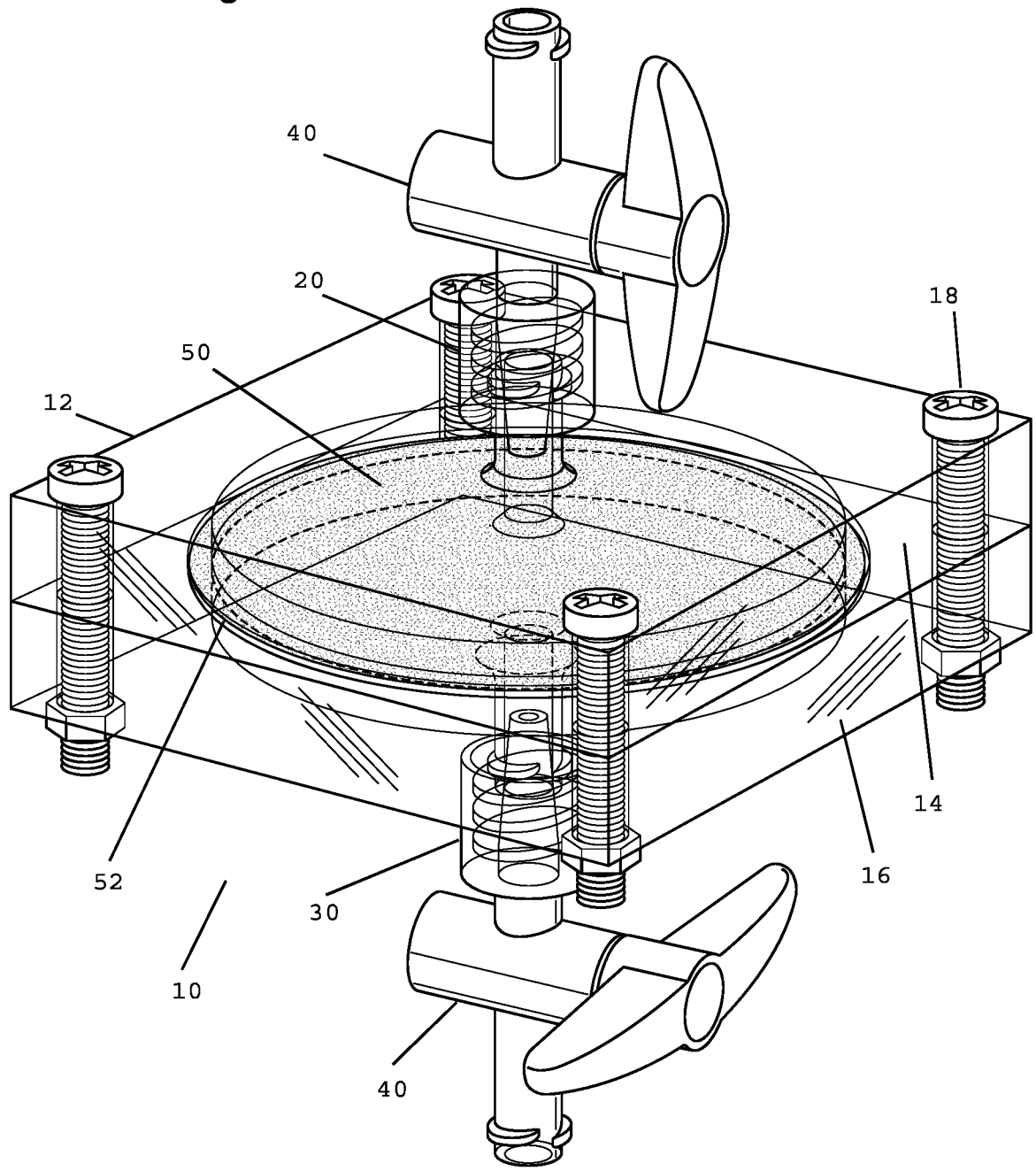
FIG. 1 illustrates a perspective view of a preferred embodiment of the apparatus of the present invention.

Tissue containing stems cells are harvested from a donor. Such extracted tissue may be taken from a source such as, but not limited to, bodily fluid, fat, bone marrow, umbilical cord and the placenta. In the case of some types of tissue such as bone marrow, the extracted tissue may be mixed with an anticoagulant such as heparin or acid citrate dextrose solution (ACD). The specific method used to harvest the tissue containing stem cells differs depending on the target location.

In the case of bone marrow, the bone marrow can be aspirated from a donor using a commercial trochar. The aspiration site, preferably at the posterior superior iliac crest of the donor, is marked upon visualization with ultrasound. An anesthetic, such as 2% Lidocaine, may be injected into the soft tissue and periosteum. An entry point through the donor's skin is created with an introducer needle, and the bone is drilled through the periosteum into the spongy bone. Using the trochar, 1 to 2 cc of bone marrow may be aspirated per level while slowly withdrawing until approximately 5 to 100 cc of bone marrow is collected in multiple syringes. Preferably, the syringes contain an anticoagulant such as heparin to mix with the extracted bone marrow.

In the case of adipose-derived aspiration, an aspiration site, preferably at the suprapubic abdominal of the donor, is marked. An anesthetic, such as 2% Lidocaine, may injected in the supramuscular space. A tumescent fluid is prepared, preferably comprising: 500 ml injectable saline, 25 cc plain 2% Lidocaine, 2 ampoules of epinephrine 1:1000, and 10 cc 8.4% sodium bicarbonate. Entry points through the donor's skin may be created with 18-gauge needles, and 60 cc of the tumescent fluid is injected slowly in the abdominal fat space. After preferably waiting 5 to 10 minutes, lipoaspiration of the fat tissue along with the tumescent fluid is conducted. Much of the tumescent fluid separates from the fat without any action required. The fat tissue may be centrifuged for about 4 minutes to separate it from the rest of the tumescent fluid. The lipoaspirate is preferably emulsified and transferred to smaller syringes.

The harvested tissue is passed through the apparatus 10 of the present invention to isolate the stem cells. Isolated stem cells may include but are not limited to mesenchymal stem cells (MSCs), hematopoietic stem cells (HSCs), pericytes, fibroblasts, tissue-specific stem cells, embryonic stem cells, induced pluripotent stem cells and others. As shown in FIGS. 1 to 10, the apparatus 10 of the present invention separates the stem cells into a stem cell collection chamber 100, while the remnants go into a remnant collection chamber 200.

Figure 2:
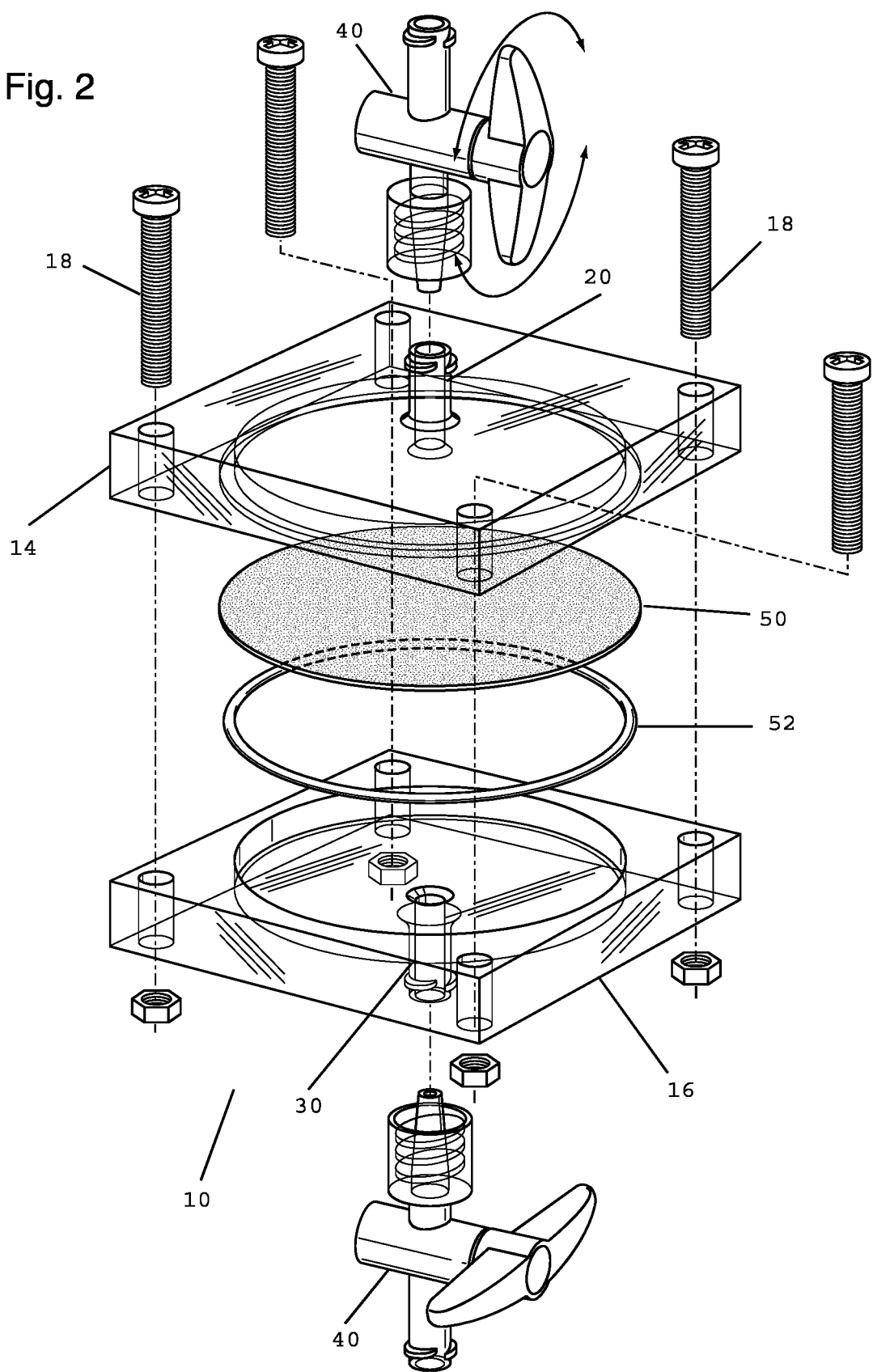
FIG. 2 illustrates an exploded view of a preferred embodiment of the apparatus of the present invention.
Figure 9:
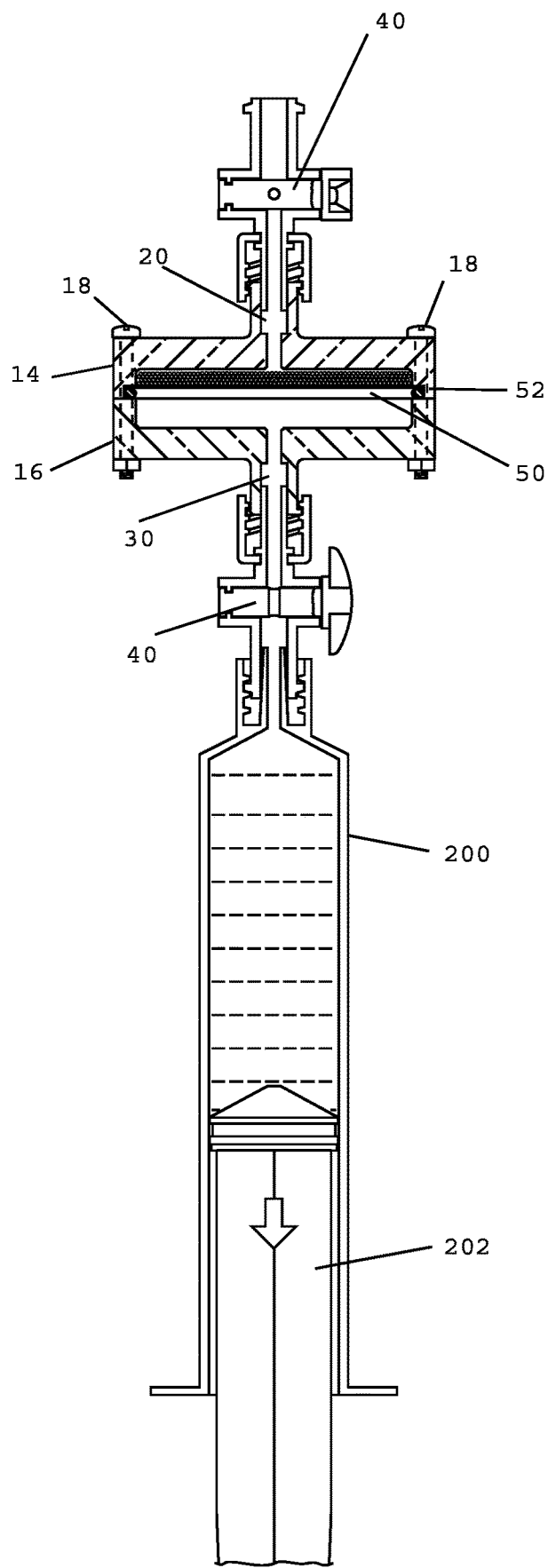
FIG. 9 illustrates a cross-sectional view of a preferred embodiment of the apparatus of the present invention where a syringe for collecting remnants is attached to the second channel and the remnants have been output from the bottom portion.
Figure 10:
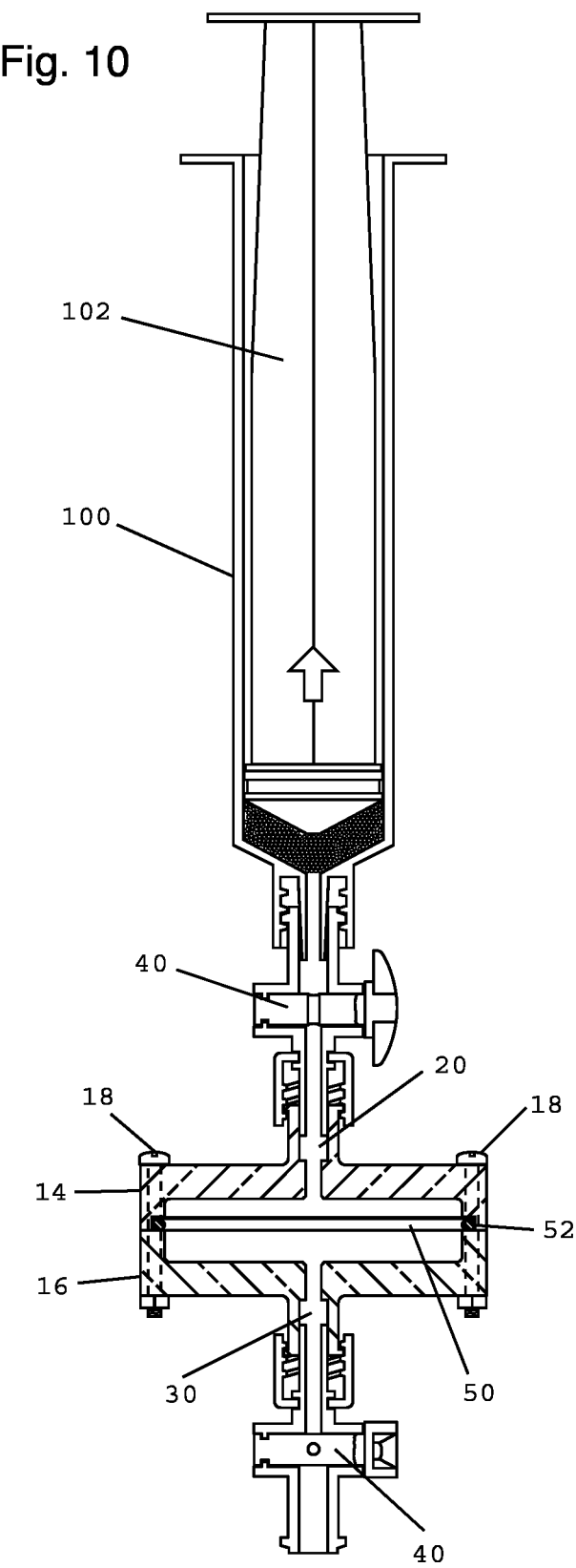
FIG. 10 illustrates a cross-sectional view of a preferred embodiment of the apparatus of the present invention where a syringe for collecting stem cells is attached to the first channel and stem cells are being output from the hollow casing.
Figure 11:
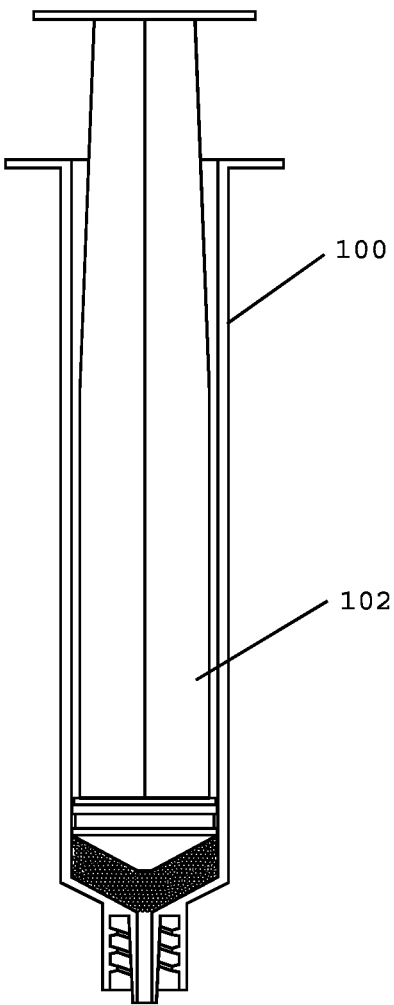
FIG. 11 illustrates a syringe which can be used with a preferred embodiment of the apparatus of the present invention.

Referring to FIGS. 1, 2 and 10, the apparatus 10 of the present invention comprises a filter 50 which captures the stem cells based on their size of generally about 8 to 10 microns (micrometers) or more, such as for example mesenchymal, hematopoetic, pericytes and fibroblasts, and sends them to a stem cell collection chamber 100. In one preferred embodiment, the stem cell collection chamber 100 forms part of a syringe, as shown in FIG. 11. Other cells in the extract pass through the filter 50 and are sent to a remnant collection chamber 200, as shown in FIG. 9.

Figure 3:
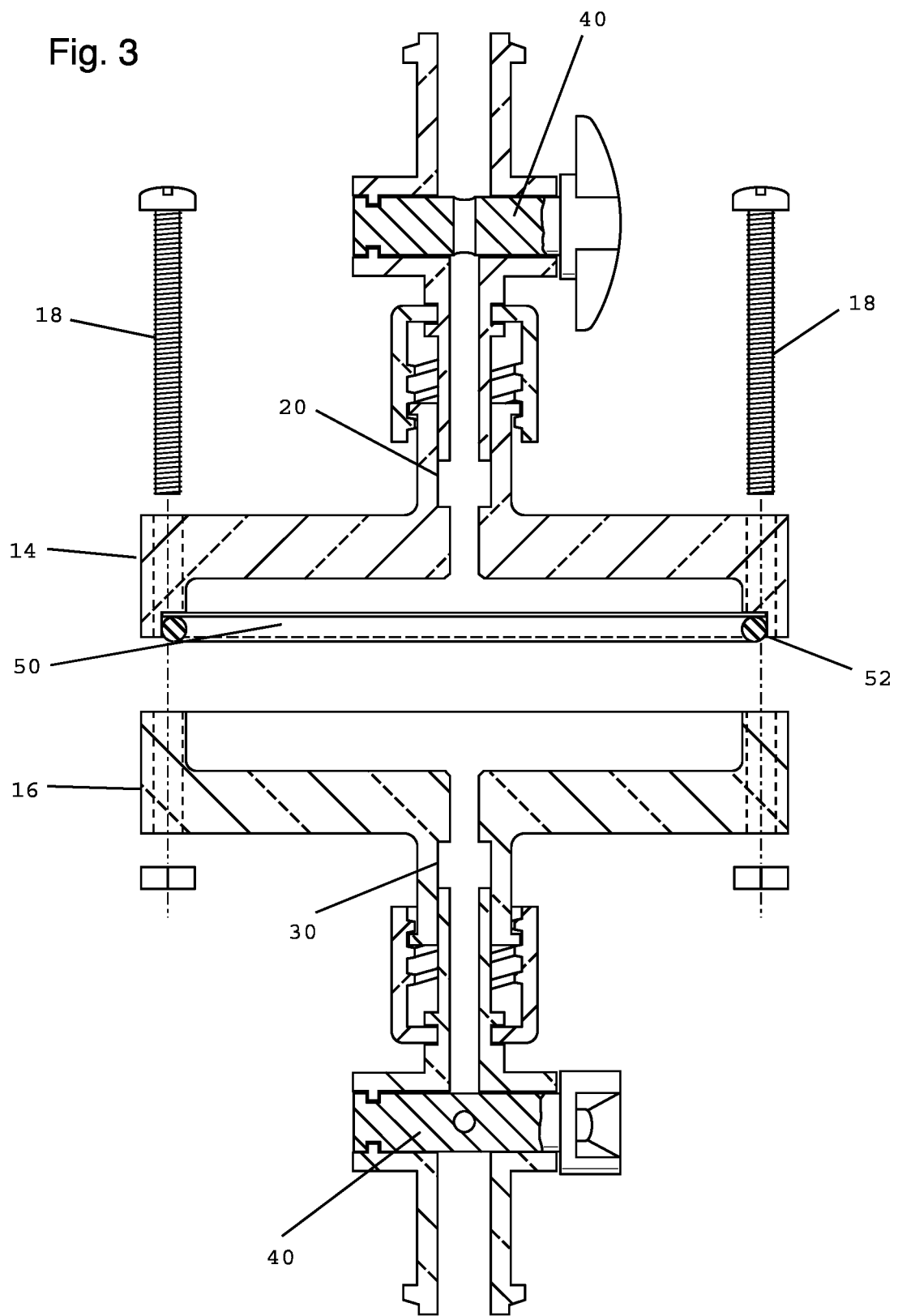
FIG. 3 illustrates a cross-sectional view of a preferred embodiment of the apparatus of the present invention where the top portion and bottom portion of the hollow casing are detached from each other.

The portable hollow casing 12 may comprise one or more of many different solid materials such as metal, glass or plastic. In one preferred embodiment which is illustrated in FIGS. 1 to 3, the hollow casing 12 comprises a top portion 14 and a bottom portion 16 which are detachable from each other. When the top portion 14 and the bottom portion 16 are detached from each other, the filter 50 (or a new or replacement filter) can be inserted between them.

With reference to FIGS. 1 to 3, the top portion 14 and the bottom portion 16 can be subsequently attached to each other, with the filter 50 housed and contained within the hollow casing 12. The top portion 14 and the bottom portion 16 of the hollow casing 12 may be attached to each other by any suitable fastening means 18, such as with screws and nuts.

Preferably, the pressure inside the hollow casing 12, more preferably in the top portion 14 of the hollow casing, is set to about 1 to 5 atm (about 14.7 psi to 73.5 psi), more preferably about 1.5 atm to 5 atm, even more preferably about 2 atm to 5 atm, even more preferably about 3 atm to 5 atm.

As best shown in FIG. 2, the filter 50 preferably comprises a nylon-based disc filter, a paper-based filter or a ceramic-based filter, which functions as a semi-permeable barrier. Preferably, the filter operates using surface filtration, where particles that cannot pass through the pores of the filter are caught on or above the filter surface.

The nylon-based disc filter, paper-based filter or ceramic-based filter is preferably manufactured to have pores that allow particles having a diameter of less than about 5 to 10 microns to pass through, more preferably less than about 5 to 8 microns, more preferably less than about 5 to 7 microns, even more preferably less than about 5 to 6 microns, even more preferably less than about 5 microns. For example, stem cells found in bone marrow generally have a diameter of about 8 to 10 microns and will not pass through but rather be captured by a filter 50 having a pore size of about 5 to 8 microns.

Preferably, the filter 50 is intended for a single use only. In alternative embodiments, the filter 50 may be used more than once.

Preferably, a barrier 52 seals and surrounds the filter 50, and separates the top portion 14 from the bottom portion 16 of the hollow casing 12. Specifically, the barrier 52 prevents any material from moving from the top portion 14 to the bottom portion 16, and vice versa, by any means other than by passing through the filter 50. No material can move around the filter 50 as it will be blocked by the barrier 52. In one preferred embodiment, the filter 50 is circular in shape and the barrier 52 is an O-ring which surrounds the filter 50. Preferably, the filter 50 is sealed using a Teflon-based O-ring 52. Teflon is a preferred material as it is a biocompatible and hydrophobic.

Figure 7:
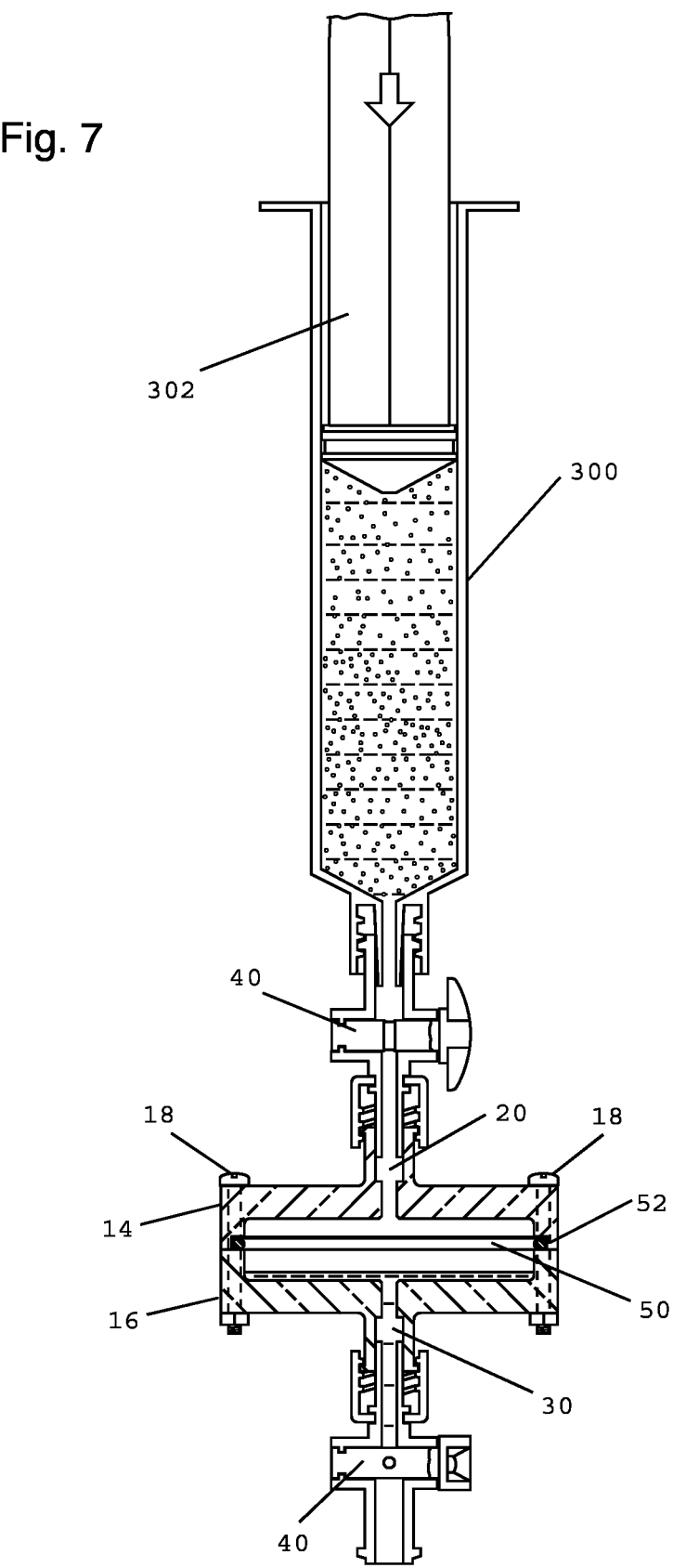
FIG. 7 illustrates a cross-sectional view of a preferred embodiment of the apparatus of the present invention where a syringe containing extracted mammalian tissue is attached to the first channel.
Figure 8:
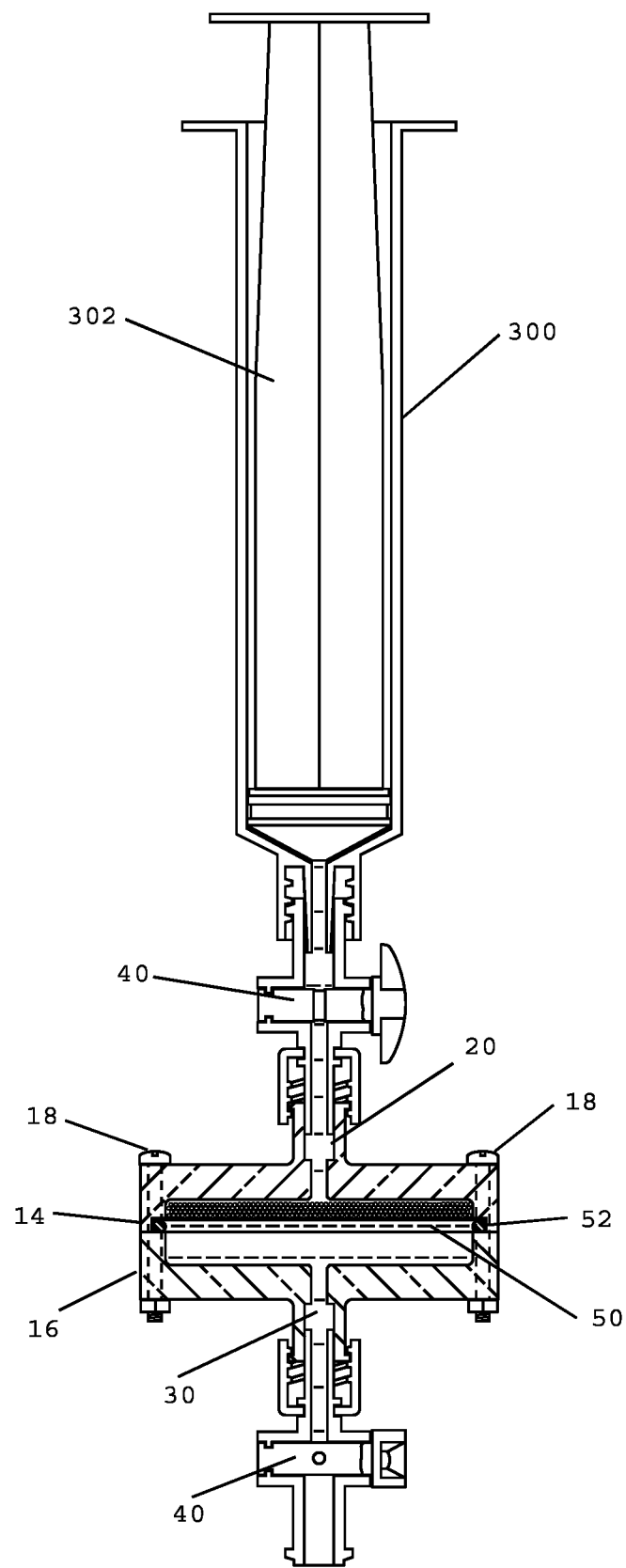
FIG. 8 illustrates a cross-sectional view of a preferred embodiment of the apparatus of the present invention where a syringe containing extracted mammalian tissue is attached to the first channel and the extracted mammalian tissue has been input into the hollow casing.

The first channel 20 is preferably positioned in the top portion 14 of the hollow casing 12. Referring to FIGS. 7 and 8, a container 300 holding the extracted mammalian tissue is preferably attachable and removable from the first channel 20. In one preferred embodiment, the container 300 holding the extracted mammalian tissue is the barrel of an extraction syringe. The extraction syringe was preferably used to harvest the mammalian tissue from the donor. By depressing the plunger or piston 302 of the extraction syringe, the extracted mammalian tissue is expelled out an opening at the front of the barrel of the extraction syringe, through the first channel 20 and into the sized internal spatial volume of the hollow casing 12. Preferably, the extracted mammalian tissue travels into the hollow casing 12 at a pressure of about 1 to 5 atm.

Inside the hollow casing 12, the extracted mammalian tissue is subjected to the filter 50. Preferably, pressure from depressing the plunger or piston 302 of the extraction syringe forces the extracted mammalian tissue to encounter the filter 50.

Particles having a diameter of about 5 to 10 microns or more are too large to pass through the filter 50. This includes the stem cells which are to be isolated. The stem cells are preferably stuck or captured in the top portion of the hollow casing 12 above the filter 50.

As illustrated in FIG. 10, a stem cell collection chamber 100 is preferably attachable and removable from the first channel 20. In one preferred embodiment, the stem cell collection chamber 100 is the barrel of a stem cell collection syringe (FIG. 11). By pulling the plunger or piston 102 of the stem cell collection syringe, the stem cells captured in the top portion 14 of the hollow casing 12 are aspirated from the hollow casing 12, through the first channel 20 and the opening at the front end of the barrel of the stem cell collection syringe, and into the barrel of the stem cell collection syringe.

Particles having a diameter of less than about 5 to 10 microns pass through the filter 50, especially when pressure from depressing the plunger or piston 302 of the extraction syringe is applied. This does not include the stem cells which are being isolated. The filtrate containing remnants pass through the filter 50 and into the bottom portion 16 of the hollow casing 12.

The second channel 30 is preferably positioned in the bottom portion 16 of the hollow casing 12. A remnant collection chamber 200 is preferably attachable and removable from the second channel 30. In one preferred embodiment shown in FIG. 9, the remnant collection chamber 200 is the barrel of a remnant collection syringe. By pulling the plunger or piston 202 of the remnant collection syringe, the remnants which passed through the filter 50 are aspirated from the hollow casing 12, through the second channel 30 and the opening at the front end of the barrel of the remnant collection syringe, and into the barrel of the remnant collection syringe.

In an alternative embodiment, the filtrate containing remnants is subjected to gravity and allowed to drip out of the hollow casing 12, through the second channel 30 and into the remnant collection chamber 200.

In one preferred embodiment, a sample of blood or blood plasma is input into the bottom portion 16 of the hollow casing 12. Preferably, the sample of blood or blood plasma is input into the bottom 16 of the hollow casing 12 prior to the extracted mammalian tissue being input into the hollow casing 12. More preferably, the sample of blood or blood plasma is taken from the same subject as the extracted mammalian tissue.

The presence of the sample of blood or blood plasma in the bottom portion 16 of the hollow casing 12 increases the efficiency of the filtration. Specifically, particles having a diameter of less than about 5 to 10 microns pass through the filter 50 and into the bottom portion 16 of the hollow casing 12 more efficiently. The sample of blood or blood plasma, or a substance in the sample of blood or blood plasma, may act as a chemoattractant and a chemical gradient forms across the filter 50. Particles having a diameter of less than about 5 to 10 microns move in the direction from a low to a high concentration of the chemoattractant, namely across the filter 50 and into the bottom portion 16 of the hollow casing 12.

In one preferred embodiment, the presence of the sample of blood or blood plasma increases the efficiency of concentrating non-hematopoetic stem cells including mesenchymal stem cells, pericytes, fibroblasts, tissue-specific stem cells, embryonic stem cells and induced pluripotent stem cells in the top portion 14 above the filter 50. Hematopoetic stem cells tend to migrate across the filter 50 and into the sample of blood or blood plasma by a natural phenomenon called chemotaxis. In particular, hematopoetic stem cells are attracted to cytokines in the sample of blood or blood plasma, such as G-CSF, SDF-1α and SLF, and migrate across the filter 50. This increases the concentration of non-hematopoetic stem cells, such as Mesenchymal stem cells, pericytes, fibroblasts, tissue-specific stem cells, embryonic stem cells, and induced pluripotent stem cells in the top portion 14 and increases the concentration of hematopoetic stem cells in the bottom portion 16.

In another preferred embodiment, a saline solution is input into the bottom portion 16 of the hollow casing 12. Preferably, the saline solution is input into the bottom portion 16 of the hollow casing 12 prior to the extracted mammalian tissue being input into the hollow casing 12.

More preferably, the saline solution is hypertonic, meaning any saline solution with a concentration of sodium chloride (NaCl) higher than physiological saline (0.9%). Preferred saline solutions include but are not limited to 2%, 3%, 5%, 7%, and 23% NaCl solutions.

The presence of the saline solution in the bottom portion 16 of the hollow casing 12 increases the efficiency of the filtration. Specifically, particles having a diameter of less than about 5 to 10 microns pass through the filter 50 and into the bottom portion 16 of the hollow casing 12 more efficiently. The saline solution may cause a high concentration of salt in the bottom portion 16, and thus causes the particles to move across more efficiently by osmosis. Specifically, the high concentration of salt promotes the flow of fluid and blood from the upper portion, across the filter 50, and to the bottom portion 16 via osmosis. Particles having a diameter of less than about 5 to 10 microns pass along with the fluid and blood through the filter 50 and into the bottom portion 16 of the hollow casing 12 more efficiently. While some prior stem cell isolation methods use saline, none of them use it for the purpose of increasing the concentration of stem cells in the other chamber.

In another preferred embodiment, both a sample of blood or blood plasma and a saline solution, preferably as a mixture, are input into the bottom portion 16 of the hollow casing 12.

Figure 4:
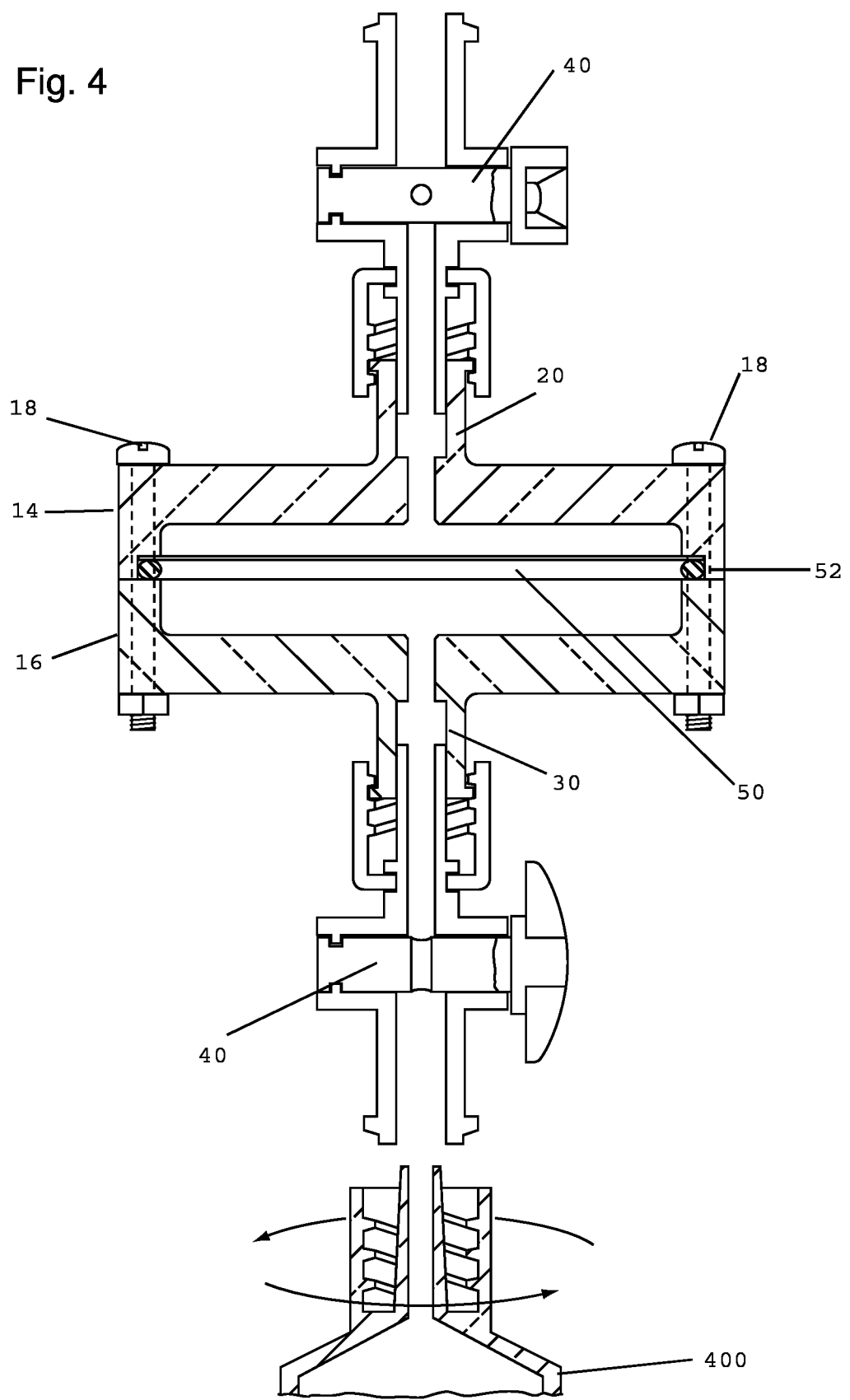
FIG. 4 illustrates a cross-sectional view of a preferred embodiment of the apparatus of the present invention where a syringe containing a sample of blood or blood plasma and/or saline solution is about to be attached to the second channel.
Figure 5:
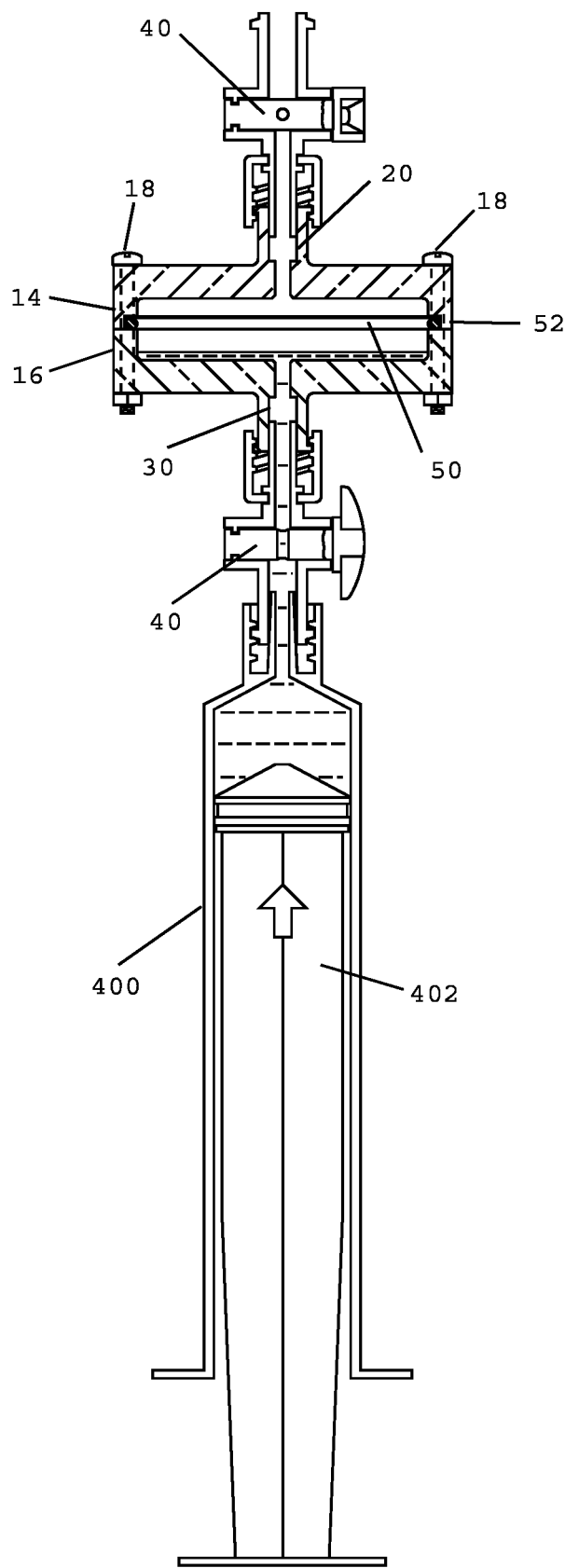
FIG. 5 illustrates a cross-sectional view of a preferred embodiment of the apparatus of the present invention where a syringe containing a sample of blood or blood plasma and/or saline solution is attached to the second channel and the sample of blood or blood plasma and/or saline solution is being input into the bottom portion.

The sample of blood or blood plasma and/or the saline solution may be input into the bottom portion 16 of the hollow casing 12 via the second channel 30. For example, as shown in FIGS. 4 and 5, a syringe 400 containing the sample of blood or blood plasma and/or the saline solution may be attached to the second channel 30. By depressing the plunger or piston 402 of the syringe 400, the sample of blood or blood plasma and/or the saline solution is expelled out an opening at the front of the barrel of the syringe 400, through the second channel 30 and into the bottom portion 16 of the hollow casing 12. Subsequently, the syringe 400 may be detached from the second channel 30 and replaced with a remnant collection chamber 300.

In a further preferred embodiment, the temperature inside the hollow casing 12 is maintained at about the normal human body temperature, more preferably at about 35 to 37 degrees Celsius. Preferably, the temperature is maintained by a heating device such as an LED light or a heating coil.

Figure 6:
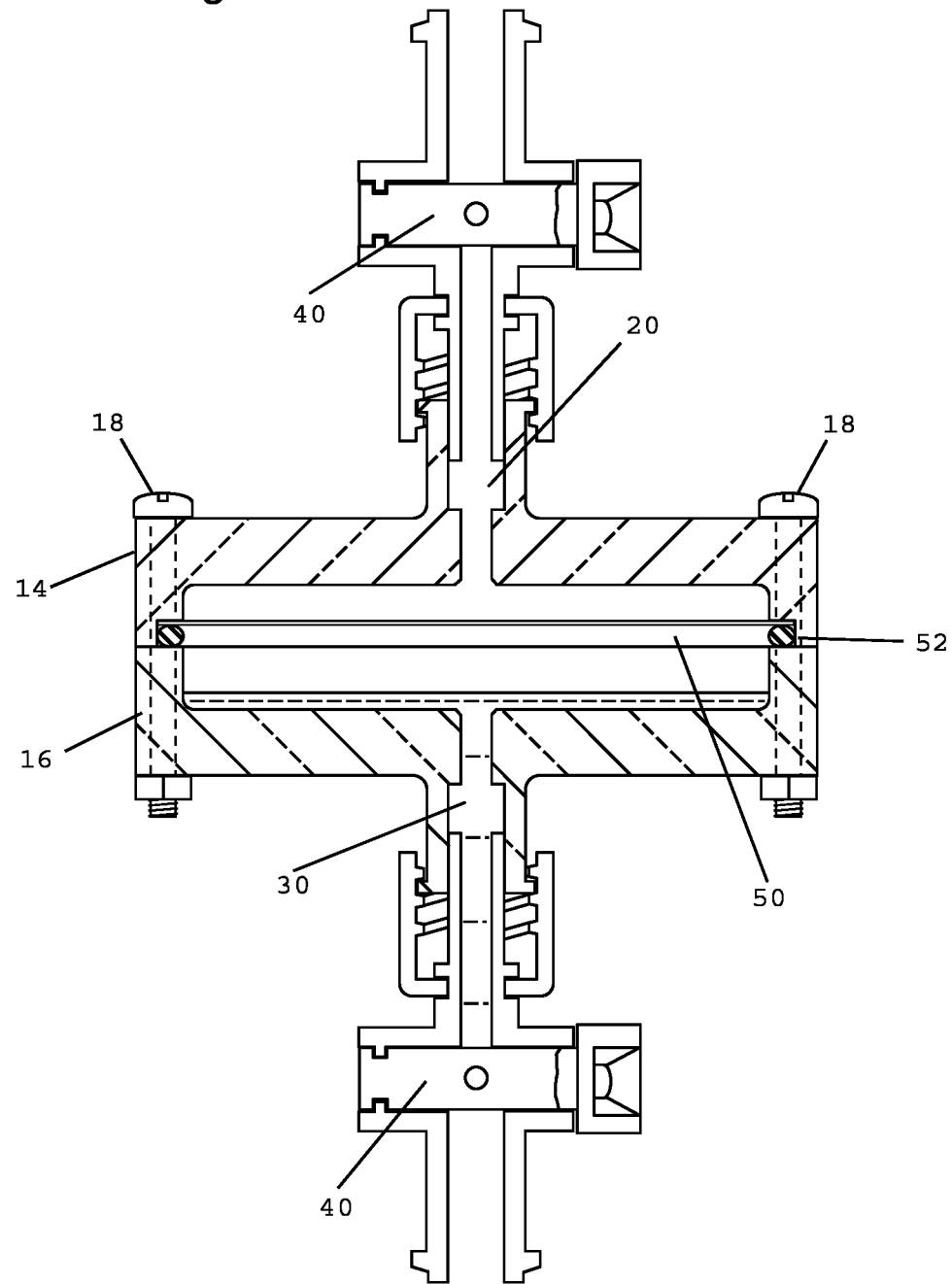
FIG. 6 illustrates a cross-sectional view of a preferred embodiment of the apparatus of the present invention with the valves at both the first channel and second channel in a closed position.

Valves 40 are preferably placed at one or more of the channels 20, 30, as well as any other opening in the portable hollow casing 12. The valves 40 prevent undesired spillage or flow of any materials to and from the hollow casing 12. The valves 40 can also work to control the pressure in the hollow casing 12 to the preferred pressure of about 1 to 5 atm. In FIG. 6, the valves 40 are shown in a closed position.

In another aspect, the present invention provides a method for isolating stem cells from extracted mammalian tissue. In one preferred embodiment as shown in FIG. 4, the valve 40 at the second channel 30 of the apparatus 10 is opened. As illustrated in FIGS. 4 and 5, a syringe 400 containing a sample of blood or blood plasma and/or saline solution is attached to the second channel 30. By depressing the plunger or piston 402 of the syringe 400, the sample of blood or blood plasma and/or the saline solution is expelled out an opening at the front of the barrel of the syringe 400, through the second channel 30 and into the bottom portion 16 of the hollow casing 12. The valve 40 at the second channel 30 is closed in order to prevent undesired spillage or flow of any materials through the second channel 30. Subsequently, the syringe 400 is detached from the second channel 30 and replaced with a remnant collection chamber 300.

Another valve 40 at the first channel 20 of the apparatus 10 is opened. Referring to FIGS. 7 and 8, a container 300 holding the extracted mammalian tissue is preferably the barrel of an extraction syringe and is attached to the first channel 20. By depressing the plunger or piston 302 of the extraction syringe, the extracted mammalian tissue is expelled out an opening at the front of the barrel of the extraction syringe, through the first channel 20 and into the sized internal spatial volume of the hollow casing 12. The valve 40 at the first channel 20 can then be closed. Subsequently, the extraction syringe is detached from the first channel 20 and replaced with a stem cell collection chamber 100.

Inside the hollow casing 12, the extracted mammalian tissue is subjected to the filter 50. Particles having a diameter of about 5 to 10 microns or more are too large to pass through the filter 50. This includes the stem cells which are to be isolated. The stem cells are preferably stuck or captured in the top portion of the hollow casing 12 above the filter 50.

Particles having a diameter of less than about 5 to 10 microns pass through the filter 50. This does not include the stem cells which are being isolated. The filtrate containing remnants pass through the filter 50 and into the bottom portion 16 of the hollow casing 12.

As mentioned above and shown in FIG. 9, a remnant collection chamber 200 is attached to the second channel 30. Preferably, the remnant collection chamber 200 is the barrel of a remnant collection syringe. The valve 40 at the second channel 30 is opened. By pulling the plunger or piston 202 of the remnant collection syringe, the remnants which passed through the filter 50 are aspirated from the hollow casing 12, through the second channel 30 and the opening at the front end of the barrel of the remnant collection syringe, and into the barrel of the remnant collection syringe. The valve 40 at the second channel 30 can then be closed.

As mentioned above and shown in FIG. 10, the stem cell collection chamber 100 is attached to the first channel 20. Preferably, the stem cell collection chamber 100 is the barrel of a stem cell collection syringe. The valve 40 at the first channel 20 is opened. By pulling the plunger or piston 102 of the stem cell collection syringe, the stem cells captured in the top portion 14 of the hollow casing 12 are aspirated from the hollow casing 12, through the first channel 20 and the opening at the front end of the barrel of the stem cell collection syringe, and into the barrel of the stem cell collection syringe. The valve 40 at the first channel 20 can then be closed.

Once the isolated stem cells are loaded into the stem cell collection syringe as illustrated in FIG. 11, the patient, who may or may not be the same person as the donor, can be treated. Chlorhexidine swabs may be used to disinfect the patient's injection site. Under guided imaging such as but not limited to ultrasound guidance or fluoroscopic guidance, the stem cells are injected into the appropriate site where treatment is required. For example, about 5 to 6 cc is injected into the knees and 8 to 10 cc injected into the hips.

The apparatus and method of the present invention provide a unique, efficient and cost-effective isolation process to select the stem cells directly.

Furthermore, the apparatus of the present invention is easy to operate, relatively small in size and easily portable. For example, a single apparatus can be moved in between and used in multiple treatment rooms or laboratory rooms of a medical clinic, or easily moved in between and used in multiple medical clinics.

EXPERIMENTAL SECTION

Protocol

Twelve 8-14 week old female C57BL/6 mice were used in the study. For the unprocessed samples, the femur and tibias of each mouse was flushed in AMEM media. The 6 Bone Marrow (BM) preparations were then washed twice by centrifugation prior to subjecting the cell pellets to red blood cell (RBC) lysis buffer. Following removal of the RBC buffer, the cell suspension was filtered using a 70 µm cell strainer then plated in 60 mm² dishes using complete AMEM media supplemented with 10% FBS and 50 U/mL Penicillin-Streptomycin. All plates were then incubated at 37° C. The media was replaced every 96 h until the end of the study.

For processed samples, the BM was collected as described above then processed using the apparatus of the present invention. Briefly, the whole marrow from the femur of a female C57BL/6 mouse was flushed in AMEM supplemented with 10% FBS, plasma lysate and 50 U/mL Penicillin-Streptomycin. The collected cells were re-suspended in 10 ml media. The device was then assembled, and 1 ml of media was passed through to wet the membrane before closing the valve at the lower part of the device. Half of the cell suspension was loaded in a 10 ml syringe and gently injected into the device. Halfway through the process the valve was opened to allow air the liquid to pass while gently injecting the remaining volume. After all the 10 ml have been injected into the device, the valve was closed. Plasma lysate was introduced, and the device placed right side up under the hood for 3-5 minutes. Finally, the enriched sample was collected by aspirating the cell suspension from the top then plated in 60 mm² dishes using complete AMEM media supplemented with 10% FBS and plasma lysate and 1% Penicillin/Streptomycin. All plates were then incubated at 37° C. The media was replaced every 96 h until the end of the study.

Results

Timeline Required to Generate a Homogenous MSC Population.

Figure 12:
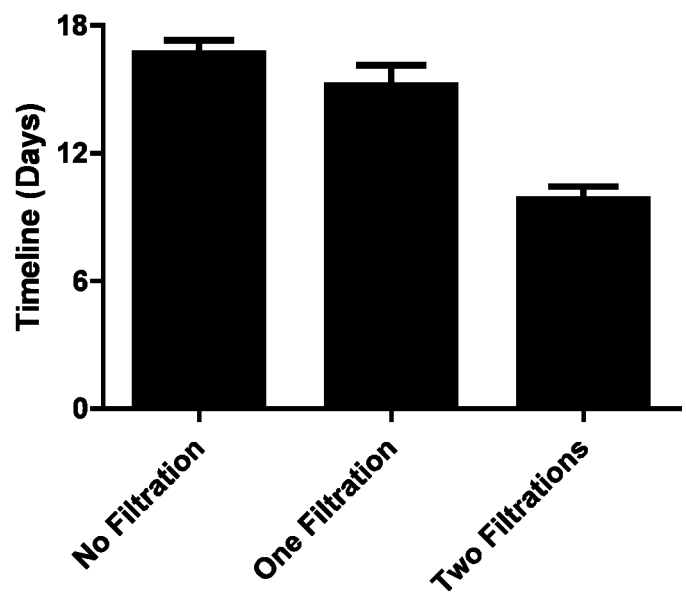
FIG. 12 illustrates a timeline for the generation of homogenous MSC populations. BM preparations isolated from wild-type female C57BL/6 mice were either plated directly or processed once or twice using the apparatus of the present invention. For this experiment, n=6/group and **P<0.01.

MSCs are normally isolated by flushing the femur and tibis of mice to collect the BM. The cell suspension is then allowed to settle down in culture plates for 3-4 days. Using this procedure, murine MSCs normally take ~3-4 weeks and 1-2 passages before reaching a completely homogenous population displaying a $CD45^-CD44^+CD73^+CD90^{-/-}CD105^{-/-}$ phenotype. Without the use of the method of the present invention, MSCs took about 16 days to reach a fully homogenous population. A single BM filtration using the apparatus of the present invention leads to a homogenous MSC population within the same timeline. Processing the BM sample twice minimized the time for MSC generation by a week or 30% (FIG. 12). Thus, multiple filtrations (>1) can significantly accelerate the generation of MSCs in vitro.

Number of MSC Colonies Generated

Figure 13:
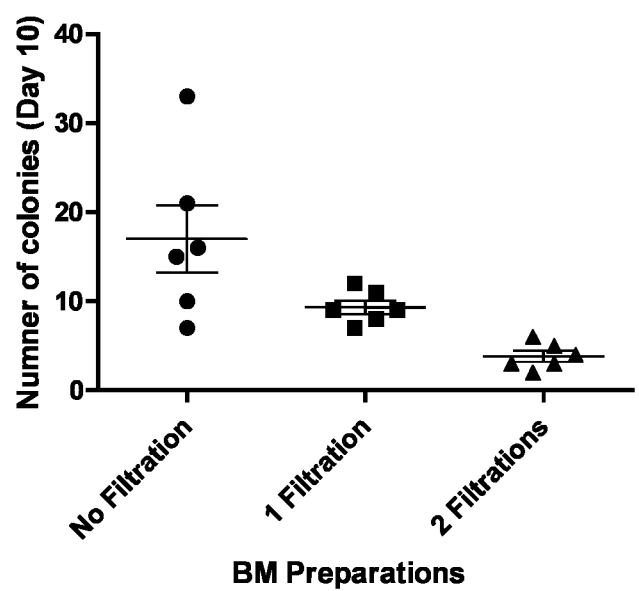
FIG. 13 illustrates an assessment of the number of MSC-like colonies at day 10 post-plating. BM preparations isolated from wild-type female C57BL/6 mice were either plated directly or processed once or twice using the apparatus of the present invention. The number of generated colonies was quantified using a contrast phase microscope. For this experiment, n=6/group and P<0.01.

The time required to generate MSCs depends heavily on the number of MSCs clones within the collected sample. Thus, we next quantified the number of MSC colonies by counting the number of foci containing cells with an MSC-like phenotype. We found that plating unprocessed MSC leads to variable colony numbers from one BM preparation to the other. In contrast, the filtration process leads to consistency as all preparations led to 9-10 colonies (FIG. 13).

Figure 14:
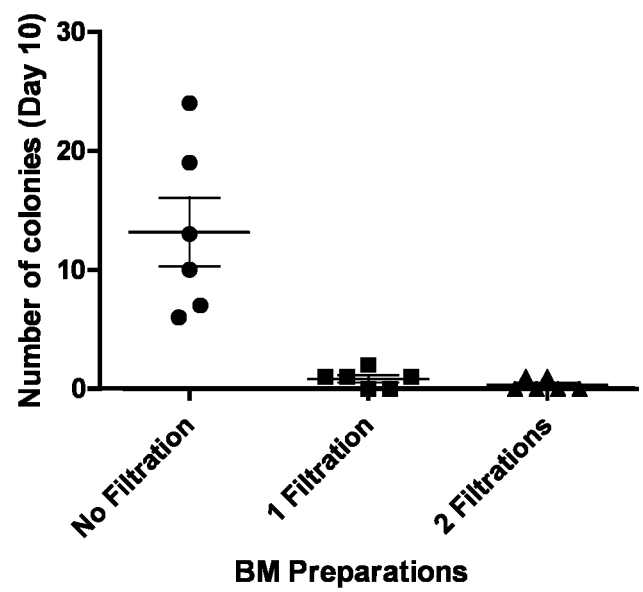
FIG. 14 illustrates an assessment of the number of MSC colonies free of "satellite cells" at day 10 post-plating. BM preparations isolated from wild-type female C57BL/6 mice were either plated directly or processed once or twice using the apparatus of the present invention. The number of generated colonies free of "satellite cells" was quantified using a contrast phase microscope. For this experiment, n=6/group and P<0.01.

Filtration Using the Apparatus of the Present Invention Leads to the Generation of "Satellite Cell-Free" Colonies Following the plating of BM preparation, colonies of various shapes and sizes form in the following 3-4 days. These colonies may contain a large number of monocytes/macrophages or even dendritic cells (e.g. mostly myeloid cells). These cells adhere in closer proximity to reach the panoply of growth factors produced by MSCs. To assess whether these "satellite cells" play a role in impeding or accelerating the rate of MSC generation, a second set of quantification was conducted on freshly isolated MSCs as described above. Interestingly, we observed almost no or little satellite cells in closer proximity to MSCs following a single or multiple device filtrations (FIG. 14). This clearly demonstrates that processing the BM preparation using the apparatus of the present invention removes efficiently most of these "satellite cells" consistent with the idea of MSC enrichment.

CONCLUSION

The main objective of the current study was to assess whether the apparatus of the present invention could be used to accelerate the generation of a homogenous MSC population. Our data clearly demonstrate that it is indeed possible as filtering the BM sample at least twice before plating minimizes the time required to obtain MSCs. Although processing the BM preparation once did not improve the time to obtain a homogenous MSC population, it consistently led to the generation of similar colony numbers that are free of "satellite cells".

While the present description is susceptible to various modifications and alternative forms, specific embodiments and implementations are shown by way of example in the drawings and will be described herein. It should be understood, however, that the description is not intended to be limited to the particular forms disclosed. Rather, the description is to cover all modifications, equivalents and alternatives falling within the spirit and scope of the invention as defined in the appended claims. The scope of the claims should not be limited by the preferred embodiments set forth in the examples but should be given the broadest interpretation consistent with the description as a whole.

The invention claimed is:

1. A method for isolating stem cells from extracted mammalian tissue comprising:
   (a) providing a container holding said extracted mammalian tissue;
   (b) attaching the container holding said extracted mammalian tissue to an apparatus for isolating stems cells from extracted mammalian tissue comprising:
   a portable hollow casing having fixed dimensions and a sized internal spatial volume;
   a filter housed and contained within said sized internal spatial volume, wherein said filter captures particles in said extracted mammalian tissue having a diameter of about 5 to 10 microns or more and allows particles in said extracted mammalian tissue having a diameter of less than about 5 to 10 microns to pass through;
   a first channel to which the container holding said extracted mammalian tissue can attach, and through which said extracted mammalian tissue is input into the hollow casing;
   wherein a stem cell collection chamber can attach to said first channel, and the particles having a diameter of about 5 to 10 microns or more are output from the hollow casing through said first channel and collected in the stem cell collection chamber; and
   a second channel to which a remnant collection chamber can attach, and through which the particles having a diameter of less than about 5 to 10 microns are output from the hollow casing and collected in the remnant collection chamber;
   wherein the hollow casing comprises a top portion and a bottom portion which are detachable from each other;
   wherein the filter is inserted between the top portion and the bottom portion;
   wherein a sample of blood or blood plasma or a saline solution is input into the bottom portion of the hollow casing via the second channel prior to the extracted mammalian tissue moving into the hollow casing;
   (c) causing the extracted mammalian tissue to move from the container holding said extracted mammalian tissue, through the first channel, into the hollow casing and into contact with the filter;
   (d) allowing particles having a diameter of about 5 to 10 microns or more to be captured by the filter, move out of the hollow casing through the first channel and into the stem cell collection chamber; and
   (e) allowing particles having a diameter of less than about 5 to 10 microns to pass through the filter, move out of the hollow casing through the second channel and into the remnant collection chamber, wherein presence of the sample of blood or blood plasma or the saline solution in the hollow casing increases efficiency of filtration of particles from the extracted mammalian tissue.

2. The method of claim 1, wherein the sample of blood or blood plasma is taken from a common subject as the extracted mammalian tissue.

3. The method of claim 1, wherein the sample of blood or blood plasma is input into the bottom portion of the hollow casing via the second channel.

4. The method of claim 1, wherein the saline solution is input into the bottom portion of the hollow casing.

5. The method of claim 4, wherein the saline solution has a salt concentration above 0.9%.

6. The method of claim 4, wherein the saline solution has a salt concentration of about 2% to 23%.

7. The method of claim 4, wherein the saline solution is input into the bottom portion of the hollow casing prior to the extracted mammalian tissue being input into the hollow casing.

8. The method of claim 4, wherein the saline solution is input into the bottom portion of the hollow casing via the second channel.

* * * * *